United States Patent [19]
Cook et al.

[11] Patent Number: 5,965,728
[45] Date of Patent: Oct. 12, 1999

[54] PROCESS FOR THE PREPARATION OF A SALT CLAVULANIC ACID

[75] Inventors: Michael Alan Cook, Laughton; Geoffrey Clive Webb, Worthington, both of United Kingdom

[73] Assignee: SmithKline Beecham PLC, Brentford, United Kingdom

[21] Appl. No.: 08/663,158
[22] PCT Filed: Jan. 31, 1995
[86] PCT No.: PCT/GB95/00191
  § 371 Date: Aug. 21, 1996
  § 102(e) Date: Aug. 21, 1996
[87] PCT Pub. No.: WO95/21173
  PCT Pub. Date: Aug. 10, 1995

[30]  Foreign Application Priority Data

Feb. 2, 1994 [GB] United Kingdom .................... 9401969

[51] Int. Cl.⁶ ........................ C07D 487/08; C07D 503/00
[52] U.S. Cl. ............................................................. 540/349
[58] Field of Search ............................................. 540/349

[56]  References Cited

FOREIGN PATENT DOCUMENTS 0 026 044  8/1980  European Pat. Off. .
0 153 843  9/1985  European Pat. Off. .

OTHER PUBLICATIONS

Chemical Abstracts; vol. 78, 19973 p. 144 abstract No. 32301.

*Primary Examiner*—Mukund J. Sham
*Assistant Examiner*—Bruce Kifle
*Attorney, Agent, or Firm*—Zoltan Kerekes; Stephen Venetianer; Charles M. Kinzig

[57]  ABSTRACT

A process for the preparation of a salt of clavulanic acid, wherein clavulanic acid in solution in a wholly or partly water-imiscible organic solvent is contacted in a region of high turbulence and/or shear stress, with a salt precursor compound to form a solution of the salt of clavulanic acid in an aqueous phase, then the organic solvent and aqueous phases are physically separated during a separation step, followed by a further processing step in which the said salt of clavulanic acid is isolated from solution as a solid.

27 Claims, 4 Drawing Sheets

PROCESS FOR THE PREPARATION OF A SALT CLAVULANIC ACID

This invention relates to a novel process for the preparation of salts of clavulanic acid.

Clavulanic acid (Z)-(2R,5R)-3-(2-Hydroxyethylidene)-7-oxo-4-oxa-1-azabicyclo[3.2.0]heptane-2-carboxylic acid) is a β-lactamase inhibitor which is used commercially as a component of pharmaceutical formulations, usually in the form of its salts. Clavulanic acid is produced commercially by culture of the microorganism *Streptomyces clavuligerus*, for example as described in GB 1508977.

Clavulanic acid or its salts may be extracted from the culture medium in various ways but normally the cells of the *S. clavuligerus* are first removed from the culture medium by such methods as filtration or centrifugation before such extraction procedures are commenced.

Clavulanic acid or its salts may be extracted from clarified culture medium by a variety of methods. Solvent extraction from cold clarified culture medium adjusted to acid pH values and methods which utilize the anionic nature of clavulanic acid at neutral pH such as the use of anion exchange resins have been found to be particularly useful. A further particularly useful method is to form an ester of clavulanic acid, purify the ester and regenerate the acid or its salt therefrom.

The extraction processes for obtaining clavulanic acid or its salts may notionally be divided into a primary isolation process followed by a further purification process.

Suitable primary isolation processes include solvent extraction of the free clavulanic acid. In the solvent extraction process the clavulanic acid is extracted into an organic solvent from cold clarified culture medium, which may be whole broth, adjusted to an acid pH value.

In one solvent extraction process for clavulanic free acid the clarified medium is chilled and the pH lowered into the region of pH 1–2 by the addition of acid while mixing with a substantially water-imiscible organic solvent. Suitable acids used to lower the pH include hydrochloric, sulphuric, nitric, phosphoric or the like mineral acids. Suitable organic solvents include n-butanol, ethyl acetate, n-butyl acetate and methyl isobutyl ketone, and other similar solvents. Methyl isobutyl ketone is a particularly suitable solvent for use in the extraction of the acidified culture filtrate. After separation of the phases clavulanic acid is found in solution in the organic phase.

The clavulanic acid may be back extracted from the organic phase into a new aqueous phase by making use of the greater water solubility of, for example, the alkali metal or alkaline earth metal salts of clavulanic acid in water than in organic solvents. Thus the clavulanic acid may be back extracted from the organic solvent into an aqueous solution or suspension of an alkali metal or alkaline earth metal base, such as sodium hydrogen carbonate, potassium hydrogen phosphate buffer or calcium carbonate, or water, while maintaining the pH at approximately neutrality, for example pH 7. This aqueous extract, after separation of the phases, may be concentrated under reduced pressure. Freeze-drying may also be employed to provide a solid crude preparation of the salt of clavulanic acid. Such solid preparations are stable when stored as a dry solid at −20° C. A similar process is described in GB 1563103. This process may be modified in known ways by for example additional purification steps applied to the organic solvent phase to remove high molecular weight impurities from the impure clavulanic acid.

A further secondary purification process for clavulanic acid is that described in for example EP 0026044, in which a solution of impure clavulanic acid in an organic solvent is contacted with t-butylamine to form the t-butylamine salt of clavulanic acid, which is then isolated, thereby separating the clavulanic acid from impurities remaining in the organic solvent, and the salt is then converted back to clavulanic acid or into a derivative of clavulanic acid such as an alkali metal salt or an ester. Other known secondary purification processes for clavulanic acid involve the use of other organic amines such as diethylamine, tri-(lower alkyl) amines, dimethylaniline and NN'-diisopropylethylenediamine to form salts and/or other derivatives thereof with the clavulanic acid. These purification process have the inherent disadvantage that they can introduce traces of the amine, or leave residual traces of salts of clavulanic acid with the amine, in the final product.

Such back extraction processes present a problem when potassium clavulanate is prepared, as potassium clavulanate is particularly water-sensitive. In conventional back extraction processes potassium clavulanate can remain in contact with water for a long time, typically around an hour or more as the solution concentration of potassium clavulanate builds up under the relatively gentle mixing and separating conditions generally used, and this can lead to extensive hydrolytic degradation.

The inventors have discovered an improved process for the preparation of salts of clavulanic acid in which degradation is reduced.

The present invention comprises a process for the preparation of a salt of clavulanic acid, wherein clavulanic acid or a labile derivative thereof in solution in a wholly or partly water-imiscible organic solvent is contacted in a contact region which is a region of high turbulence and/or shear stress, with a salt precursor compound of a salt forming cation with a counter anion in solution or suspension, the counter anion being capable of exchange with clavulanate anion, in the presence of water, such that a solution of the salt of clavulanic acid in an aqueous phase is formed, then the organic solvent and aqueous phases are physically separated during a separation step, followed by a further processing step in which the said salt of clavulanic acid is isolated from solution as a solid.

Suitable salts of clavulanic acid preparable by this process include alkali metal and alkaline earth metal salts. A particularly preferred salt is potassium clavulanate, being that widely used in pharmaceutical formulations in which clavulanate functions as a β-lactamase inhibitor.

Suitable organic solvents include those described above, for example n-butanol, ethyl acetate, n-butyl acetate, and ketones of the general formula $R^1 CO.R^2$ where $R^1$ and $R^2$ are independently $C_{1-10}$ alkyl groups, in particular methyl isobutyl ketone. The solution of clavulanic acid may contain impurities, for example high molecular weight impurities such as may be present if the solution has been obtained by a primary isolation process as described above, but preferably has been subjected to a preliminary purification process to remove at least some of the impurities. Suitable preliminary purification processes include filtration, and treatment with absorbent carbon. The solution may also contain small quantities of dissolved or suspended water, but preferably if the solution has been obtained from a primary isolation process it may be subjected to a dewatering process, for example centrifuging to remove droplets of suspended water.

A suitable solution concentration for the solution of clavulanic acid or its labile derivative is around 500 to 20,000 μg/ml (0.0025M to 0.1M), for example around 1,000–5,000 μg/ml (i.e. 0.005M to 0.025M), typically around 3,000±1,000 µg/ml (i.e. 0.015 M ±0.005 M) expressed in terms of clavulanic acid content. Suitable labile derivatives of clavulanic acid include readily-cleaved esters, such as silyl esters. The term "clavulanic acid" as herein after used refers to both free clavulanic acid and such labile derivatives.

Suitable salt forming cations are alkali metal cations and alkaline earth metal cations, in particular potassium. Suitable counter anions include basic anions, such as hydrogen carbonate, carbonate or hydrogen phosphate, and in particular anions of weak organic carboxylic acids, such as those of formula $R—CO_2H$ where R is $C_{1-20}$ alkyl, for example $C_{1-8}$ alkyl. Suitable carboxylic acids include acetic, propionic and ethyl hexanoic, such as 2-ethyl hexanoic acid.

Suitable salt precursor compounds including these ions are sodium or potassium hydrogen carbonate, potassium hydrogen phosphate or calcium carbonate, and particularly in the case of preparation of potassium clavulanate, potassium 2-ethyl hexanoate. Other suitable salt precursor compounds include ion-exchange resins, which may be solid or liquid, and which incorporate a salt-forming cation such as potassium which can form a salt with clavulanic acid.

The clavulanic acid or derivative may be contacted in solution with the salt precursor compound by dissolving or suspending the precursor compound in a solvent, and mixing the two solutions or the solution and suspension. The same organic solvent may be used for the clavulanic acid and the precursor. In the case of potassium 2-ethyl hexanoate as salt precursor compound such a solution in an organic solvent such as methyl isobutyl ketone may suitably be 0.5 to 5.0 M, e.g. 1.0 to 3.0 M, suitably 2.0±0.5M in potassium 2-ethyl hexanoate.

Water may be provided in the contact region in a number of ways as discussed below, and one or more of these ways may be used as alternatives or together. For example the salt precursor compound may itself be dissolved or suspended in water or water containing dissolved organic solvent, and contacted as such with the solution of clavulanic acid. For example the solution of clavulanic acid may contain dissolved or suspended water, e.g. as mentioned above. For example the salt precursor compound may be dissolved or suspended in an organic solvent, e.g. the same solvent as the clavulanic acid is dissolved in, and these solvents may itself include dissolved or suspended water. For example methyl isobutyl ketone may be used as such an organic solvent for the clavulanic acid and the precursor, and may include 0.1 to 7.5% v:v of dissolved water, typically 1 to 3%, e.g. 2.0±0.5%. For example water may be provided by adding water or an aqueous medium such as water containing dissolved organic solvent to the clavulanic acid solution and solution or suspension of the salt precursor in an organic solvent, as they are brought into contact in the contact region.

When dissolved water is present in the organic solvents used in the process of the invention, e.g. as described above, it may subsequently separate out as the aqueous phase by a "salting out" effect as it accumulates the dissolved clavulanic acid salt.

The working conditions, e.g. concentrations of reactants, relative proportions of solutions used, flow rates, contact times etc., of the process are selected such that inter alia as much as possible of the clavulanic acid is extracted from the solution in the organic solvent into the aqueous phase as the solution of its salt, and such that a concentrated solution of the salt of clavulanic acid in the aqueous phase is formed. In the case of potassium clavulanate, in a preferred embodiment working conditions are selected so as to produce a concentration of potassium clavulanate in the aqueous phase of ca. 10 to 40 weight % (ca. 0.4 to 1.7 M), for example 20 to 30 weight % (ca. 0.8 to 1.2 M). A solution concentration of potassium clavulanate of this concentration is found to expediate the further processing step, with an optimised yield and improved purity.

In the process, monitoring of the concentration of the clavulanic acid salt such as potassium clavulanate in the separated aqueous phase, for example by density, optically etc. is a suitable way of determining and controlling the other working conditions.

The clavulanic acid and the salt precursor compound should be introduced such that there is an initial stoichometric excess of the salt precursor compound over the clavulanic. For example the precursor may be introduced in a 1:1.1 to 1:2 molar ratio clavulanic acid:precursor compound, typically 1:1.1 to 1:1.5, to ensure that there is theoretically sufficient salt precursor compound to combine with all of the clavulanic acid in the region of contact.

The amount of water present in the region in which the clavulanic acid and salt precursor compound are brought into contact should suitably be around the minimum necessary to in practice achieve a desired aqueous phase concentration of the salt, for example as discussed above for potassium clavulanate.

In the contact region it is desirable to achieve as rapid and efficient contact between the components, i.e. clavulanic acid solution, salt precursor compound solution and water present either in the organic solvents or introduced into the contact region as a separate phase, as possible. It is desirable that in the contact region any water and/or aqueous phase which is present as a separate phase is present in a form which has a high surface contact area with the organic phase, and for example the aqueous phase may be a dispersed emulsion phase, i.e. broken up into a form such as small droplets so as to create a high contact surface area between the two phases.

Efficient contact between the components may suitably be achieved using known mixing devices which provide a high degree of fluid turbulence and shear stress in the contact region where liquids introduced into the mixer mix, and which are capable of breaking up a separate water or aqueous phase into small droplets. Such mixers are known in the art, and selection of a suitable mixing device to achieve this will be apparent to those skilled in the art. The above-mentioned components may each be introduced separately into the contact region, or alternatively they may be pre-mixed or blended upstream of the contact region and then introduced into the contact region together.

Suitable mixing devices include known in-line mixers, e.g. of the type in which one or more turbulence-creating elements are located within a pipeline during which the components are caused to flow. Another suitable type of mixer is a homogeniser, e.g. of the type in which two liquid phases are forced a pressure through a biased valve. Suitable mixing devices may also include cavities subjected to high turbulence and or shear stress by means of turbines, propellers etc.

Another and preferred type of mixer is a chamber wherein introduced fluids are subjected to intense rotational swirling, for example a vortex chamber of the type disclosed generally in EP-0153843-A (UK Atomic Energy Authority, the contents of which are incorporated herein by reference), the vortex chamber comprising a chamber of substantially circular cross section, e.g. generally cylindrical in shape, and having at least one tangential inlet and an axial outlet. In such a mixer the components are fed in via the tangential inlet(s) and experience swirling resulting in thorough mixing. The components may be fed in via a single tangential inlet if they are already in admixture before entry into the vortex chamber, or may each be fed in through a separate tangential inlet, to mix in the vortex chamber.

The mixing procedure described above results in formation of an emulsion of fine droplets of the aqueous phase comprising an aqueous solution of the salt of clavulanic acid dispersed in a bulk phase of organic solvent. The aqueous and solvent phases are then physically separated in the separation step. Separation may be carried out using known separation devices, in particular centrifugal separators. A suitable type of centrifugal separator is a disc centrifuge. Such disc centrifuges generally consist of a chamber of generally circular internal section within which is a central disc stack, and a void space between the outer edge of the disc stack and the walls of the chamber. In view of the high ratio of organic phase to aqueous phase used in the process of this invention, as discussed above, it is desirable that the void space is relatively small. The construction and operation of such a centrifuge will be well known to those skilled in the art.

The emulsion may be fed from the mixing device directly to the separation device, preferably with as short a transfer time as possible so as to minimise hydrolytic degradation of salts such as potassium clavulanate. Alternatively, a mixer of the type described in EP-153843-A may be used, which comprises a vortex chamber as described above and having a combined separator stage which comprises a column forming an extension of the outlet and having, at or adjacent its end remote from the vortex chamber, spaced apart openings whereby fluids of different densities introduced into the chamber through the inlet(s) swirl through the chamber and the swirling flow from the chamber in passing along the column results in centrifugal separation of the fluids with the separated fluids emerging from the column through the spaced apart openings.

Using the components and mixing and separating devices as discussed above, the components may be fed into the mixing device and the emulsion of organic and aqueous phases which is formed in the mixing device may be fed into the separation device, the aqueous phase emerging as a separated phase from the separation device. The relative ratios of components fed into the mixing device will vary with conditions, principally the concentration of and solvent used for the clavulanic acid solution. In determining these ratios, as mentioned above it is preferred to monitor the concentration of the salt of clavulanic acid in the aqueous phase emerging from the separation device, and adjust the input of salt precursor compound and if necessary any added water accordingly as determined by experiment to achieve and maintain the desired concentration.

Typically when using the concentrations of clavulanic acid and potassium 2-ethyl hexanoate discussed above, the volume ratio of water:organic solvent in the contact region may be in the range 1:50 to 1:300, for example 1:150 to 1:250, suitably around 1:180±20. Suitably this ratio of water may be achieved by introducing additional water at a suitable flow rate of water into the contact region, or alternatively by removing excess water by a suitable conventional dewatering technique.

For example using the typical concentrations of clavulanic acid in methyl isobutyl ketone, and concentrations of potassium 2-ethyl hexanoate in methyl isobutyl ketone/water described above, to produce the typical potassium clavulanate concentrations in the aqueous phase discussed above, the relative volume ratios of clavulanic acid solution:potassium 2-ethyl hexanoate solution:water introduced into the mixing device may be around 180±25:2±0.2:1±0.2. The absolute volumes used will of course depend upon the sizes of mixing and separation devices used and the quantity of clavulanic acid solution available, e.g. from a primary isolation process.

The conditions of high turbulence and/or shear stress in the contact region enable the process of the invention to be carried out extremely rapidly, such that when potassium clavulanate is prepared in the process the time the aqueous phase need be in contact with the organic phase, and consequently the time the potassium clavulanate is in aqueous solution need be very short. The total time that the organic phase and aqueous phase are in contact may be less than one hour. Preferably the organic phase and aqueous phase are in contact for substantially less than this time, suitably 15 minutes or less, more preferably 10 minutes or less, more preferably 5 minutes or less, ideally as little a time as possible whilst also achieving a suitable degree of transfer of clavulanate ion from the organic phase into the aqueous phase as its salt. Suitably the time the components of the process are in contact in the contact region and the separation stage may be 0.5 to 3 minutes, for example the residence time of the organic phase in the contact region may be 0.5 to 2.0 minutes, e.g. 1 minute ±15 seconds, and the residence time in the separation stage may suitably be 1.5 to 3.0 minutes, e.g. 2 minutes ±15 seconds. The time the components are in the contact region and separation stage of the process can depend upon the scale of the process, but the general principles and specific process details set out in this disclosure provide guidance to those skilled in the art to set up a process suitable for industrial scale use.

During the course of the process of this invention, transfer of clavulanate ion from the organic solution phase to the aqueous phase occurs. Some formation of the salt of clavulanic acid will occur whilst the phases are in contact whilst undergoing separation in the separation stage. As explained above it is preferred that this transfer occurs as quickly as possible. Suitably more than 75%, preferably more than 80%, e.g. 90% or more of the clavulanate ion transfers from the organic phase during the time the organic phase and the aqueous phase are in contact during the contact and separation stages of the process. The extraction of this proportion of the clavulanate ion into the aqueous phase is a measurable property of the process, and can be used as a control parameter to control for example the input of the components.

The output of the separation step of the process is a concentrated aqueous solution of the salt of clavulanic acid, e.g. potassium clavulanate, which may also contain dissolved organic solvent, unused salt precursor compound and other impurities etc., together with a separate organic solvent phase output containing residual clavulanic acid in solution. This depleted solution of clavulanic acid in organic solvent may be subjected in a two or more stage process of this invention for a second and optionally subsequent time to the mixing and separation stages of the process of the present invention as described above, to extract a further proportion of the clavulanic acid as the salt. Suitably in this way 90% or more of the total initial clavulanic acid in solution in the organic solvent may be extracted into the aqueous phase as the salt of clavulanic acid, for example 93% or more, typically 96–98%. The extraction of this overall proportion of the clavulanic acid is again a measurable property of the aqueous phase and may be used as a control parameter as outlined above.

In one embodiment of such a two-stage process the aqueous phase output of the separation step of the second stage, comprising an aqueous solution of the salt of clavulanic acid and unreacted residual salt precursor compound, e.g. respectively potassium clavulanate and potassium 2-ethyl hexanoate, may be fed back into the contact region of the first stage of the process as a source of the aqueous medium.

In such a case, salt precursor compound and any additional water may be introduced into the contact region of the second stage, and there may be no need for an initial direct input of salt precursor compound and/or water into the contact region of the first stage of the process. In the process of this embodiment sufficient salt precursor compound should be added to provide a stoichiometric excess over the clavulanic acid present in both contact regions and separation steps. In the two-stage process of this embodiment, the output of aqueous phase solution of the salt of clavulanic acid is collected from the separation step of the first stage of the process.

The concentrated aqueous solution of the salt of clavulanic acid obtained as the output from the separation stage of the invention whether the process is single or multi-stage is subjected to a further processing stage to isolate the salt of clavulanic acid as a solid, preferably as crystals of the salt product, e.g. of potassium clavulanate. Although the aqueous solution may be subjected to known processes such as freeze-drying to isolate the solid, it is preferred to admix the aqueous solution with an organic solvent, optionally with chilling to precipitate the salt from solution in a crystalline form. In the case of potassium clavulanate isopropyl alcohol is a suitable organic solvent for the purpose of precipitating crystals.

Whatever further processing procedure is used it is desirable to subject the aqueous solution of the salt of clavulanic acid to this further processing procedure as soon as possible, so as to minimise hydrolytic degradation of the salt, particularly of potassium clavulanate. Suitably therefore the entire process from initial contact between the clavulanic acid or its labile derivative to precipitation of a crystalline salt product takes less than one hour. The aqueous solution may for example be run directly from the output of the separation stage, e.g. of a centrifugal separator, and mixed with an organic solvent to cause precipitation of crystals. For example an output of concentrated aqueous potassium clavulanate solution may be run into an excess of organic solvent, e.g. chilled isopropanol.

Optionally the aqueous solution may be further purified, e.g. by treatment with granular charcoal followed by filtration, and this purification may be carried out on the aqueous solution before or after admixing with an organic solvent in a crystal precipitation step. The crystals formed may be isolated by conventional means, e.g. filtration followed by drying.

The process of the invention may be operated as a continuous or semi-continuous process or as a batch process.

The process of this invention provides salts of clavulanic acid, for example potassium clavulanate, free of the trace impurities introduced by known purification processes, such as the amines used in the purification process mentioned above. Although salts of clavulanic acid free of such impurities are known on a laboratory scale, the bulk production of such salts, in particular potassium clavulanate, for use in the preparation of pharmaceutical formulations is novel.

Consequently a further aspect of this invention provides a pharmaceutical formulation for the treatment of bacterial infections which comprises a salt of clavulanic acid, e.g. as described above, in particular potassium clavulanate, the formulation being substantially free of organic amines such as t-butylamine, diethylamine, tri-(lower alkyl) amines, methylaniline or NN'-diisopropylethylene diamine (either as free amines or as derivatives or salts thereof).

Suitably the formulation contains less than 0.05%, for example less than 0.005%, preferably less than 0.0005%, desirably less than 0.00005% of organic amines by weight with respect to the weight of the clavulanic acid salt present in the formulation.

The formulation may also comprise one or more antibiotic compounds, suitably β-lactam antibiotics such as penicillins and cephalosporins. Suitable antibiotics include the antibiotics with which clavulanic acid is combined in known antibiotic formulations, for example amoxycillin (e.g. in the form of its trihydrate) and ticarcillin. The formulation may comprise ratios of clavulanic acid salt:antibiotic within the known ranges in which such combinations are used, e.g. 12:1 to 1:1 by weight expressed as in terms of the parent clavulanic acid and antibiotic.

The formulation may also contain other known additives and excipients, e.g., fillers, binders, disintegrants, an effervescent couple, colourants, flavourings, desiccants etc., for example those listed for use with formulations containing potassium clavulanate in GB 2005538. The formulation may also contain materials such as cellulose derivatives, e.g. microcrystalline celluloses such as Avicel (Trade Mark) or Syloid (Trade Mark), silicon dioxide or sucrose together with potassium clavulanate. The formulation may for example comprise a blend of potassium clavulanate with a cellulose derivative, silicon dioxide or sucrose, for example in a 1:1 weight ratio.

The invention also provides a process for the use of a salt of clavulanic acid being substantially free of organic amines, as described above, in the manufacture of a pharmaceutical formulation for the treatment of bacterial infections.

The invention will now be described by way of example only with reference to the accompanying drawings, in which.

Figure 1A:
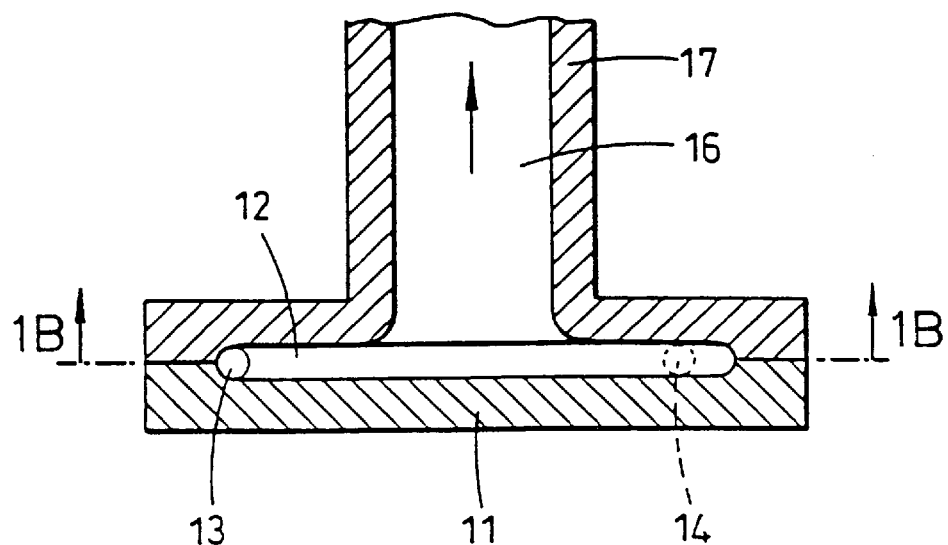
FIG. 1 shows a mixing device in the form of a vortex chamber having three tangential inlets and an axial outlet.
Figure 1B:
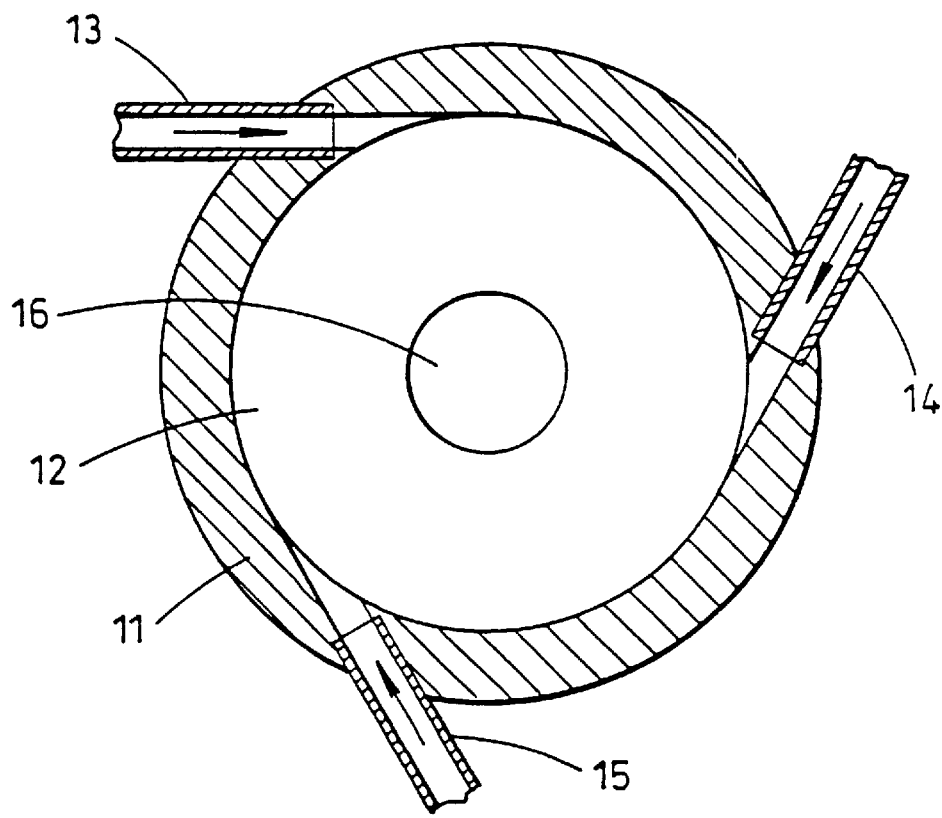

Referring to FIG. 1, a vortex chamber, shown overall (11), consisting of an essentially cylindrical chamber (12), having respective first, second and third tangential inlets (13), (14), (15) and a single axial outlet (16) is shown in a part-sectional side-on view in FIG. 1A, and in a sectional plan view through the plane A—A of FIG. 1A, in FIG. 1B. In operation first, second and third liquids (not shown) are introduced at speed through the respective first, second and third tangential inlets (13), (14), (15) in the direction of the arrows shown and a vortex is formed within the chamber (12) in which the first, second and third liquids mix. The flow of mixed first, second and third liquids leaves the chamber (12) in the direction shown by the arrow via the axial outlet (16), formed in a tubular extension (17) of the walls of chamber (12).

Figure 2:
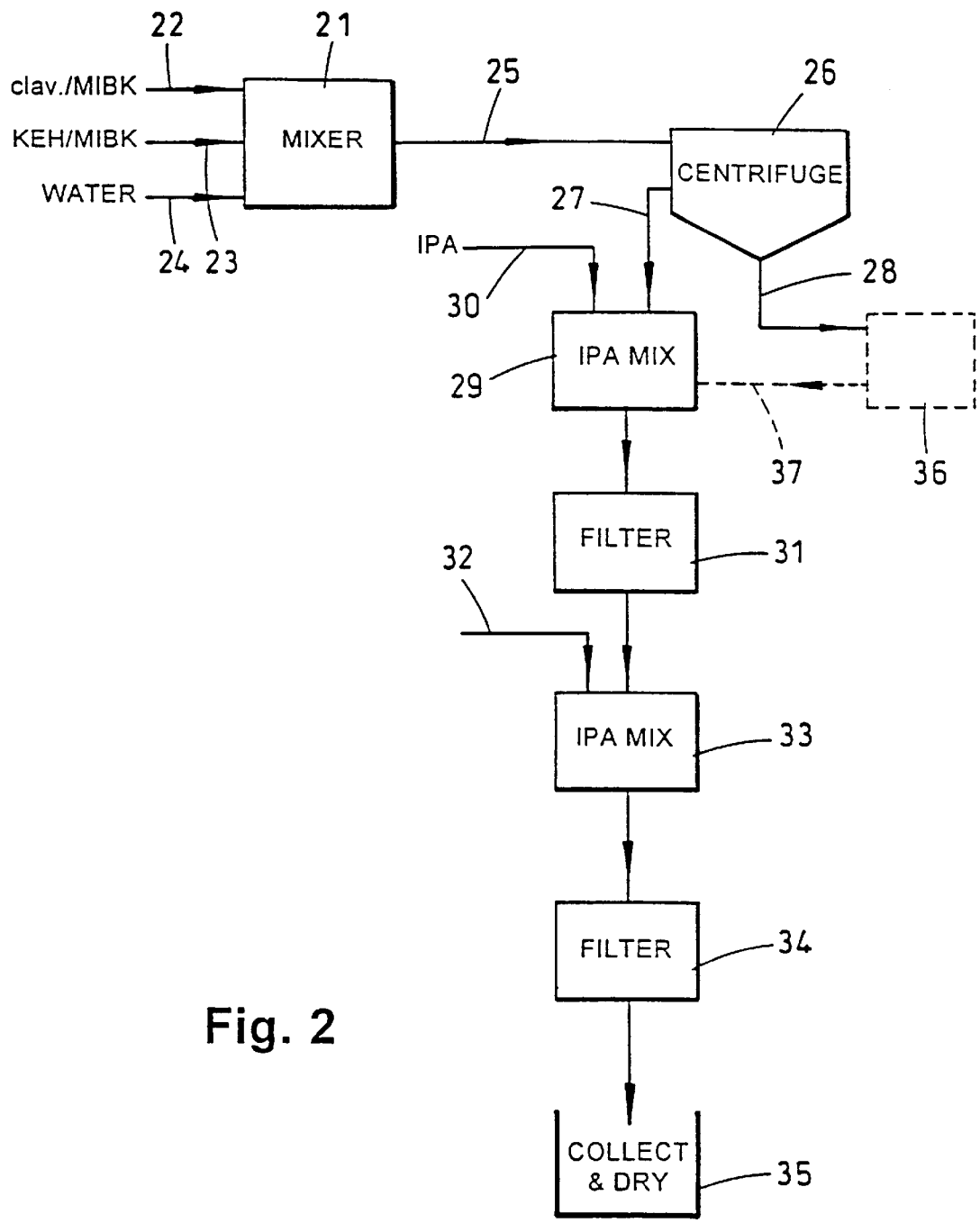
FIG. 2 shows an overall schematic diagram of a single-stage process of the invention.

Referring to FIG. 2, into a vortex chamber (21) of the type shown in FIG. 1 is introduced a flow of a solution of clavulanic acid in methyl isobutyl ketone, of concentration about 3000 μg/ml, via a first tangential inlet (22). Via a second tangential inlet (23) is introduced a flow of a solution of potassium 2-ethyl hexanoate, in methyl isobutyl ketone +2% v:v water of concentration about 2M in potassium 2-ethyl hexanoate. Through a third tangential inlet (24) is introduced a flow of water.

The internal diameter of the vortex chamber (21) is about 10 cm, and its height about 2.5 cm. The respective flow rates through (22), (23) and (24) are around 3.5 L, 34 ml and 18 ml per minute, the volume of potassium 2-ethyl hexanoate solution added via (23) being such as to maintain a 1.3:1 molar excess of ingoing potassium 2-ethyl hexanoate to clavulanic acid.

Under the swirling conditions inside the vortex chamber (21) thorough mixing of the respective components introduced via inlets (22), (23) and (24) occurs, and the water is broken up into an emulsion of fine droplets. The residence time of the mixture in the vortex chamber (21) is about 1 minute. At the end of this time the emulsion exits from the axial outlet (16) of mixer (21) and is transferred via line (25) into centrifugal separator (26).

Centrifugal separator (26) is a commercial disc centrifuge modified by an internal essentially toroidal insert (not shown) that minimises the internal void space between the disc stack and the inner wall of the casing. The centrifugal separator (26) separates the organic solvent phase and the aqueous phase, the former emerging via exit (27), the latter via exit (28). The residence time in the centrifuge (26) is about 2 minutes.

The concentration of potassium clavulanate in the solution emerging from (27) is monitored, e.g. by density, and is used to control the input rate of water through inlet (24), the flow being decreased if concentration drops, and vice versa. An optimum concentration of ca. 20–25 wt % of potassium clavulanate in the solution emerging from (27) is sought. The concentrated aqueous solution emerging from (28) is transferred into tank (29) containing a four volume excess of isopropyl alcohol, (added via inlet 30) until an equivalent of 25 g of clavulanic acid has been collected in tank (29). Granular absorbent carbon (ca. 10–20 wt. % of liquid) is then added and the mixture in tank (29) is stirred for 5 minutes. A further volume of isopropyl alcohol is then added to tank (29) via inlet (30) and the mixture stirred for a further 20 minutes. The granular carbon is then removed by celite filtration in filter (31), the filter bed being then washed with a minimum quantity of a 7:1 isopropyl alcohol:water mixture.

The filtrate is then run into 2.5 L of isopropyl alcohol (added via inlet 32) in tank (33) to crystallise the potassium clavulanate. The slurry of crystals and mother liquor in tank (33) is stirred and cooled to 3–5° C. over 1 hour. The crystals are then isolated by filtration in filter (34) before collection and vacuum drying (35). The yield of the process is about 90% based upon the initial clavulanic acid present in solution in the methyl isobutyl ketone input solution entering at (22).

It will be understood that two or more combinations of mixer (21) and centrifugal separator (26) may be arranged in parallel to increase throughput through the process of this invention.

In a modification of the procedure shown in FIG. 2 to provide a two-stage process, the output of organic solvent phase from outlet (28) may be fed into a further combination (36) of mixer (21) and centrifugal separator (26) via the axial outlet (16) of the further mixer (21), and further potassium 2-ethyl hexanoate solution and water may be introduced via the respective tangential inlets (23), (24) of the further mixer (21). This results in separation of a further portion of an aqueous phase comprising a concentrated solution of potassium clavulanate which can be combined via (37) with the potassium clavulanate solution obtained from the first stage of the process, in tank (29), and subjected to the further treatment steps outlined above. By operating the process as a two stage process in this way the yield can be improved to ca. 96–98%.

Figure 3:
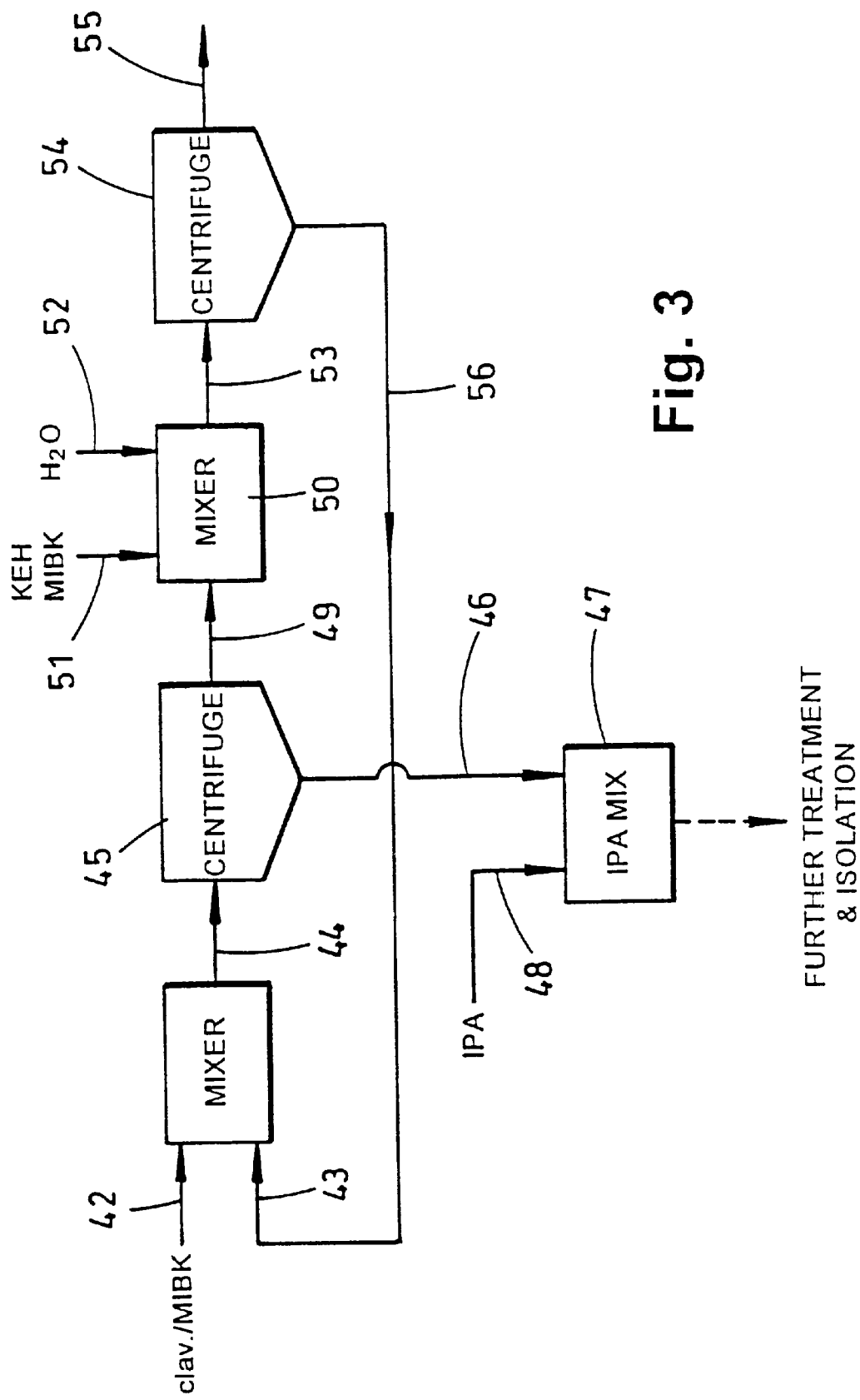
FIG. 3 shows an overall schematic diagram of a two-stage process of the invention.

In a further two-stage modification of the above process, shown in FIG. 3, into a vortex mixer (41) of the type shown in FIG. 1 but having two tangential inlets (42), (43) is introduced a flow of a solution of clavulanic acid in methyl isobutyl ketone, of concentration about 3000 $\mu$g/ml, via tangential inlet (42) at a flow rate of about 3.5 L per minute. Into tangential inlet (43) is introduced an aqueous flow obtained from a subsequent step of the process, to be described below. The dimensions of the vortex mixer (41) are similar to those of vortex mixer (21).

The dwell time of the mixture in mixer (41) is about 1 minute, at the end of this time the emulsion produced exits from axial outlet (16) of mixer (41) and is transferred via line (44) to centrifugal separator (45), of construction similar to separator (26). The residence time of the mixture in centrifugal separator (45) is about 2 minutes. The aqueous phase output from centrifuge (45), comprising a concentrated aqueous solution of potassium clavulanate is transferred via line (46) to tank (47) corresponding to tank (29) of FIG. 2, where it may be admixed with isopropyl alcohol, introduced via line (48) and subjected to further treatment and isolation steps identical to those (30–35) shown in FIG. 2.

The organic phase output from centrifuge (45), comprising a depleted solution of clavulanic acid in methyl isobutyl ketone is transferred via line and axial inlet (49) into a second mixer (50) similar to mixer (41). Through tangential inlets (51, 51) are introduced respectively flows of potassium 2-ethyl hexanoate solution in methyl isobutyl ketone (ca. 2M, flow rate ca. 34 ml per minute) and water (flow rate ca. 18 ml per minute). The residence time of the mixture in mixer (50 is about 1 minute.

The emulsion from the axial outlet (16) of mixer (50) is passed via line (53) to centrifugal separator (54), similar to separator (45), the residence time in separator (54) being about 1 minute. The organic solvent phase emerges from the separator (54) via line (55). The aqueous phase emerges from the separator (54) as an aqueous solution of potassium clavulanate and residual potassium 2-ethyl hexanoate, and is fed back via line (56) into tangential inlet (43) of mixer (41) as the aqueous phase input mentioned above.

The concentration of potassium clavulanate in the solution emerging from (46) is monitored, as in the process described above, and is used to control the input of water through inlet (52), an optimum concentration of about 20–25 wt. % of potassium clavulanate in the aqueous solution being sought.

The overall yield of the process of FIG. 3 is about 96–98% based upon the initial clavulanic acid present in the solution entering at (42).

Figure 4:
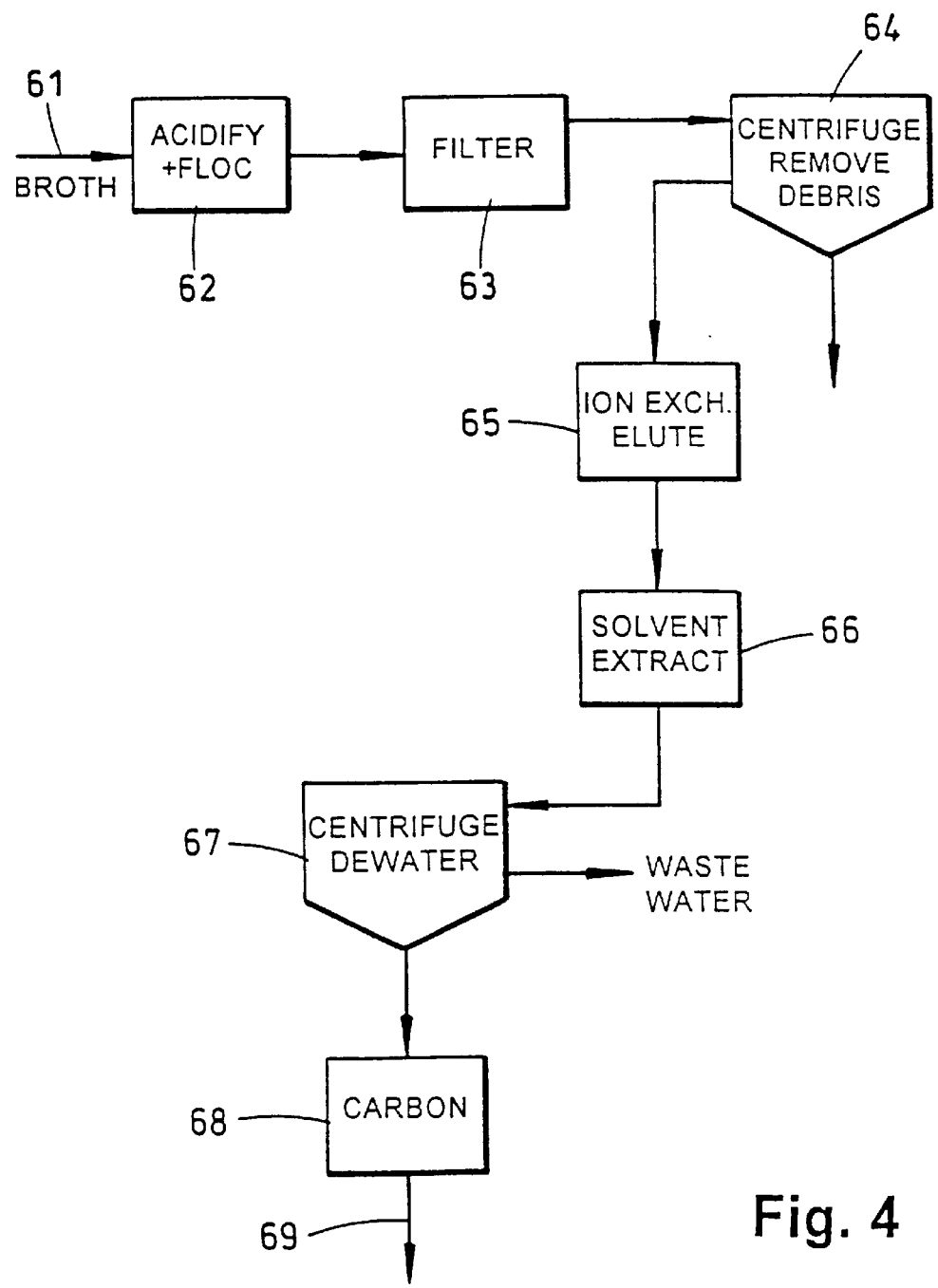
FIG. 4 shows a schematic diagram of a primary isolation process for clavulanic acid.

Referring to FIG. 4, a process is shown schematically whereby crude fermentation broth from a culture of *S. clavuligerus* may be used to prepare a solution of clavulanic acid in organic solvent of suitable quality for use in the process of this invention.

Crude broth is passed via (61) into tank (62) where it is acidified with acetic acid and mixed with flocculent, The mixture is then filtered in rotary vacuum filter (63) and centrifuged in centrifuge (64) to remove remaining solid debris. The clavulanic acid is then adsorbed on a ion exchange resin column (65) and eluted off as a more concentrated, e.g. 1500–50000 $\mu$g/ml, e.g. 5000–50000 $\mu$g/ml, aqueous solution. Suitable ion exchange resins and elution conditions are for example as described in GB 1563103 This aqueous solution is then extracted in extractor (66) into an organic solvent such as methyl isobutyl ketone. This organic solution of clavulanic acid may then be dewatered using centrifuge (67) and passed through an absorbent carbon bed (68) before emerging at (69) in a form suitable for use as the feedstock of the above processes at (22) or (42) shown in FIGS. 2 and 3.

We claim:

1. A process for the preparation of a salt of clavulanic acid, wherein clavulanic acid in solution in a wholly or partly water-imiscible organic solvent is contacted in a contact region which is a region of high turbulence and/or shear stress, with a salt precursor compound of a salt forming cation with a counter anion in solution or suspension, the counter anion being capable of exchange with clavulanate anion, in the presence of water, such that a solution of the salt of clavulanic acid in an aqueous phase is formed, then the organic solvent and aqueous phases are physically separated during a separation step, followed by a further processing step in which the said salt of clavulanic acid is isolated from solution as a solid.

2. A process according to claim 1 wherein the salt is potassium clavulanate.

3. A process according to claim 1 wherein the organic solvent is n-butanol, ethyl acetate, n-butyl acetate, or ketones of the general formula $R^1C(O)R^2$ wherein $R^1$ and $R^2$ are independently $C_{1-10}$ alkyl groups.

4. A process according to claim 3 that wherein the organic solvent is methyl isobutyl ketone.

5. A process according to claim 1 wherein the concentration of the clavulanic acid solution is around 500 to 20,000 µg/ml (0.0025M to 0.1M) in clavulanic acid.

6. A process according to claim 1 wherein the counter anion of the salt precursor compound is hydrogen carbonate, carbonate or hydrogen phosphate, or anions of weak organic carboxylic acid of formula $R—CO_2H$ wherein R is $C_{1-20}$ alkyl.

7. A process according to claim 6 wherein the salt precursor compound is sodium or potassium hydrogen carbonate, potassium hydrogen phosphate or calcium carbonate, or potassium 2-ethyl hexanoate.

8. A process according to claim 1 wherein the salt precursor compound is contacted with the solution of clavulanic acid by dissolving or suspending the precursor compound in a solvent, and mixing the two solutions or the solution and suspension.

9. A process according to claim 8 wherein potassium 2-ethyl hexonoate is the salt precursor and is used in solution in an organic solvent at a solution concentration of 0.5 to 5.0 M in potassium 2-ethyl hexanoate.

10. A process according to claim 8 wherein water is provided in the contact region by the salt precursor compound being dissolved or suspended on water containing dissolved organic solvent, and contacted as such with the solution of clavulanic acid.

11. A process according to claim 10 wherein the water is provided in the contact region by the solution of clavulanic acid containing dissolved or suspended water.

12. A process according to claim 1 wherein water is provided in the contact region by the salt precursor compound being dissolved or suspended in an organic solvent and the solvent include dissolved or suspended water.

13. A process according to claim 12 wherein methyl isobutyl ketone is used as an organic solvent for the clavulanic acid and the precursor, and includes 0.1 to 7.5% v:v of dissolved water.

14. A process according to claim 1 wherein water is provided in the contact region by adding water to the clavulanic acid solution and solution or suspension of the salt precursor in an organic solvent, as they are brought into contact in the contact region.

15. A process according to claim 1 wherein the working conditions of the process are selected such that inter alia as much as possible of the clavulanic acid is extracted from the solution in the organic solvent into the aqueous phase as the solution of its salt, and such that a concentrated solution of the salt of clavulanic acid in the aqueous phase is formed.

16. A process according to claim 15 wherein the salt of clavulanic acid is potassium clavulanate and the concentration of potassium clavulanate in the aqueous phase is ca. 10 to 40 weight % (ca. 0.4 to 1.7M).

17. A process according to claim 1 wherein the volume ratio of water:organic solvent in contact region is in the range 1:50 to 1:300.

18. A process according to claim 1 wherein contact between the components is achieved using an in-line mixer of the type in which one or more turbulence-creating elements are located within a pipeline during which the components are caused to flow, or a homogeniser or in a vortex chamber of the type comprising a chamber of substantially circular cross section and having at least one tangential inlet and an axial outlet, or in a cavity in which intense turbulence and/or shear stress are produced by a turbine or propeller.

19. A process according to claim 1 the clavulanic acid salt produced is potassium clavulanate, and the salt precursor is potassium 2-ethyl hexonoate used in solution in methyl isobutyl ketone, and water is added into the mixing region, the relative volume ratios of clavulanic acid solution:potassium 2-ethyl hexonoate solution:water introduced into the mixing device may be around 180±25:2±0.2:1±0.2.

20. A process according to claim 1 wherein the total time that the organic phase and aqueous phase are in contact is 1 hour or less.

21. A process according to claim 20 wherein the salt of clavulanic acid being prepared is potassium clavulanate and the potassium clavulanate remains in aqueous solution for 1 hour or less.

22. A process according to claim 1 more than 75% of the clavulanate ion transfers from the organic phase during the time the organic phase and the aqueous phase are in contact.

23. A process according to claim 1 wherein the output of depleted organic solvent phase containing residual clavulanic acid in solution is subjected in a two or more stage process for a second and optionally subsequent time to the mixing and separation stages of the process as claimed in claim 1, to extract a further proportion of the clavulanic acid as the salt.

24. A process according to claim 23 wherein the two-stage process the aqueous phase output of the separation step of the second stage, comprising an aqueous solution of the salt of clavulanic acid and unreacted residual salt precursor compound is fed back into the contact region of the first stage of the process as a source of the aqueous medium.

25. A process according to claim 24 wherein the salt precursor compound and additional water is introduced into the contact region of the second stage.

26. A process according to claim 23 wherein the aqueous of the salt of clavulanic acid obtained as the output from the separation stage of the invention is admixed with an organic solvent and optionally chilled to precipitate the salt form solution to crystals.

27. A process according to claim 26 wherein the salt of clavulanic acid is potassium clavulanate and the organic solvent with which the aqueous solution is admixed is isopropyl alcohol.

* * * * *